US00PP35981P3

(12) United States Plant Patent
Hofmann

(10) Patent No.: US PP35,981 P3
(45) Date of Patent: Jul. 9, 2024

(54) ***MANDEVILLA* PLANT NAMED 'INMANBEWHI22'**

(50) Latin Name: *Mandevilla sanderi*
Varietal Denomination: Inmanbewhi22

(71) Applicant: INNOVAPLANT ZIERPFLANZEN GmbH & Co. KG, Gensingen (DE)

(72) Inventor: Birgit Hofmann, Rudesheim am Rhein (DE)

(73) Assignee: INNOVAPLANT ZIERPFLANZEN GmbH & Co. KG, Gensingen (DE)

( * ) Notice: Subject to any disclaimer, the term of this patent is extended or adjusted under 35 U.S.C. 154(b) by 0 days.

(21) Appl. No.: 18/384,486

(22) Filed: Oct. 27, 2023

(65) Prior Publication Data

US 2024/0164231 P1 May 16, 2024

Related U.S. Application Data

(60) Provisional application No. 63/425,462, filed on Nov. 15, 2022.

(51) Int. Cl.
*A01H 5/02* (2018.01)
*A01H 6/08* (2018.01)

(52) U.S. Cl.
USPC ..... Plt./232
CPC ..... *A01H 6/088* (2018.05)

(58) Field of Classification Search
USPC ..... Plt./232
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Mandevilla* plant named 'Inmanbewhi22', characterized by its broadly upright plant habit; moderately vigorous to vigorous growth habit and moderate growth rate; freely branching habit; dense and bushy appearance; dark green-colored leaves; early and freely flowering habit; and pure white-colored flowers with yellow-colored throats.

2 Drawing Sheets

Figure 1:
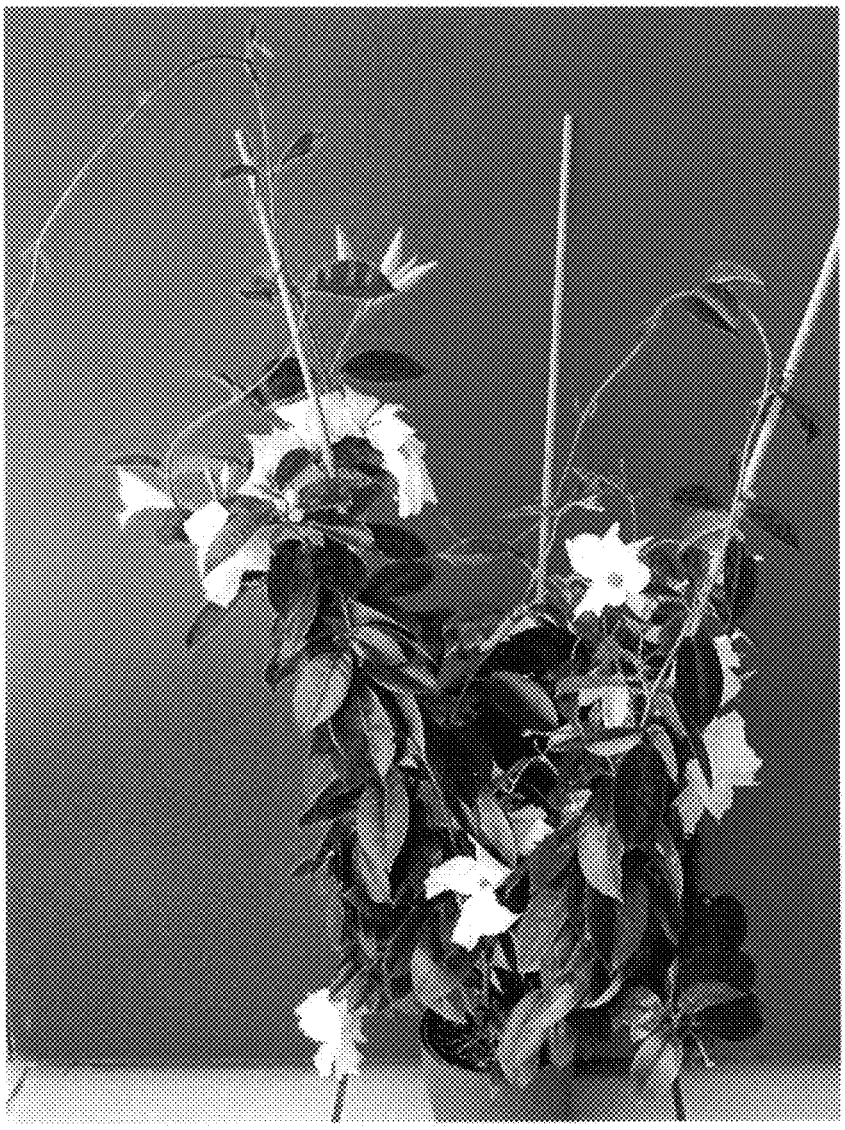

Botanical designation: *Mandevilla sanderi*.
Cultivar denomination: 'INMANBEWHI22'.

STATEMENT REGARDING PRIOR DISCLOSURES BY INVENTOR and APPLICANT/ASSIGNEE

An European Community Plant Breeder's Rights application for the instant plant was filed by the Applicant/Assignee of the instant application, Innovaplant Zierpflanzen GmbH & Co. KG of Gensingen, Germany on Oct. 24, 2022, application number 2022/2396. Foreign priority is not claimed to this European Community Plant Breeder's Rights application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Mandevilla* plant, botanically known as *Mandevilla sanderi* and hereinafter referred to by the name 'Inmanbewhi22'.

The new *Mandevilla* plant is a product of a planned breeding program conducted by the Inventor in Johannesburg, South Africa and Heidesheim, Germany. The objective of the breeding program is to create new freely branching *Mandevilla* plants that flower early and freely and have attractive flowers that resist fading and sunscalding.

The new *Mandevilla* plant originated from a cross-pollination conducted by the Inventor in Johannesburg, South Africa in November, 2016 of a proprietary breeding selection of *Mandevilla sanderi* identified as code number D14-3242-2, not patented, as the female, or seed parent with a proprietary breeding selection of *Mandevilla sanderi* identified as code number D14-3163-2, not patented, as the male, or pollen, parent. The new *Mandevilla* plant was discovered and selected by the Inventor as a single flowering plant from within the progeny of the stated cross-pollination in a controlled greenhouse environment in Heidesheim, Germany in June, 2018.

Asexual reproduction of the new *Mandevilla* plant by vegetative cuttings in a controlled greenhouse environment in Heidesheim, Germany since June, 2018 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Inmanbewhi22'. These characteristics in combination distinguish 'Inmanbewhi22' as a new and distinct *Mandevilla* plant:

1. Broadly upright plant habit.
2. Moderately vigorous to vigorous growth habit and moderate growth rate.
3. Freely branching habit; dense and bushy appearance.
4. Dark green-colored leaves.
5. Early and freely flowering habit.
6. Pure white-colored flowers with yellow-colored throats.

Plants of the new *Mandevilla* can be compared to plants of the female parent selection. Plants of the new *Mandevilla* differ primarily from plants of the female parent selection in the following characteristics:

1. Leaves of plants of the new *Mandevilla* are longer, narrower and lighter green in color than leaves of plants of the female parent selection.
2. Plants of the new *Mandevilla* flower earlier than plants of the female parent selection.
3. Flowers of plants of the new *Mandevilla* are pure white in color with yellow-colored throats whereas plants of the female parent selection are yellow in color with white-colored stripes.

Plants of the new *Mandevilla* can be compared to plants of the male parent selection. Plants of the new *Mandevilla* differ primarily from plants of the male parent selection in the following characteristics:

1. Plants of the *Mandevilla* are not as freely branching as plants of the male parent selection.
2. Leaves of plants of the new *Mandevilla* are lighter green in color than leaves of plants of the male parent selection.
3. Flower petals of plants of the new *Mandevilla* are not as undulate as flower petals of plants of the male parent selection.
4. Flower throats of plants of the new *Mandevilla* are lighter yellow in color than flower throats of plants of the male parent selection.

Plants of the new *Mandevilla* can also be compared to plants of *Mandevilla sanderi* 'Inmanwhimp', disclosed in U.S. Plant Pat. No. 28,276. In side-by-side comparisons, plants of the new *Mandevilla* differ primarily from plants 'Inmanwhimp' in the following characteristics:

1. Plants of the new *Mandevilla* are not as freely branching as plants of 'Inmanwhimp'.
2. Leaves of plants of the new *Mandevilla* are broader and darker green in color than leaves of plants of 'Inmanwhimp'.
3. Plants of the new *Mandevilla* flower about one week earlier than plants of 'Inmanwhimp'.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet (FIG. 1) is a side perspective view of a typical flowering plant of 'Inmanbewhi22' grown in a container.

Figure 2:
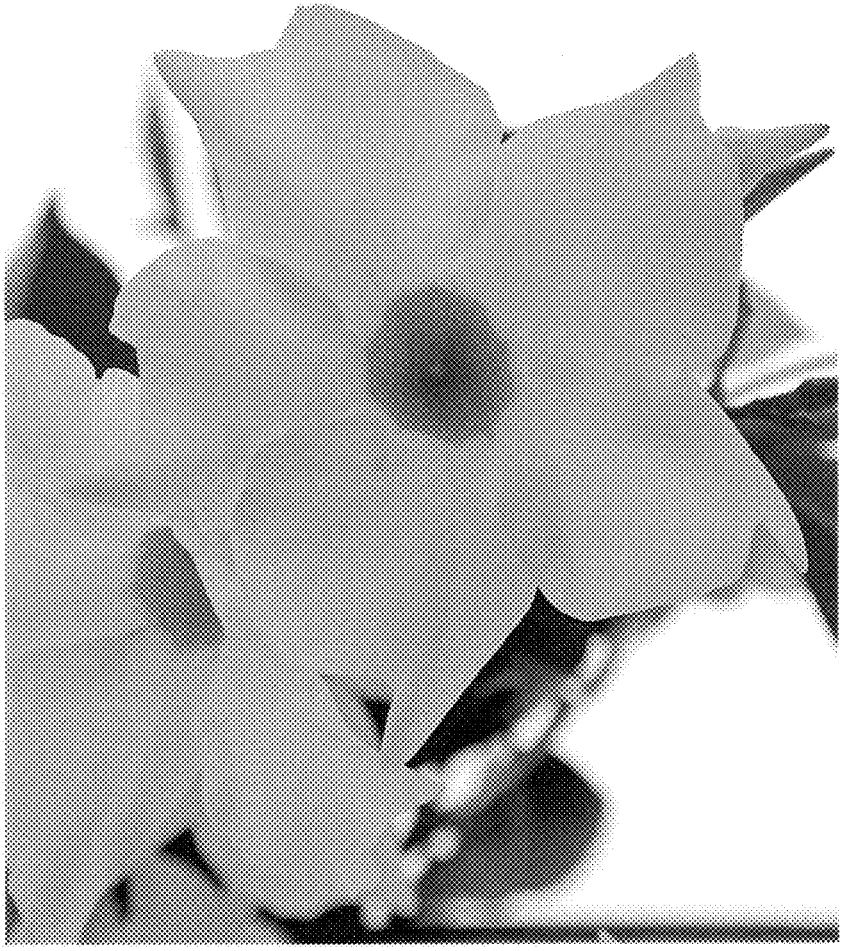

The photograph on the second sheet (FIG. 2) is a close-up view of typical flowers of 'Inmanbewhi22'.

DETAILED BOTANICAL DESCRIPTION

The aforementioned photographs and following observations, measurements and values describe plants grown during the summer in 11-cm containers in a glass-covered greenhouse in Heidesheim, Germany and under cultural practices typical of commercial *Mandevilla* production. During the production of the plants, day temperatures ranged from 12C to 35C and night temperatures ranged from 12C to 18C. Plants were four months old when the photographs and description were taken. In the following description, color references are made to The Royal Horticultural Society Colour Chart, 2015 Edition, except where general terms of ordinary dictionary significance are used.

Botanical classification: *Mandevilla sanderi* 'Inmanbewhi22'.

Parentage:

*Female, or seed, parent.*—Proprietary breeding selection of *Mandevilla sanderi* identified as code number D14-3242-2, not patented.

*Male, or pollen, parent.*—Proprietary breeding selection of *Mandevilla sanderi* identified as code number D14-3163-2, not patented.

Propagation:

*Type.*—By vegetative cuttings.

*Time to initiate roots, summer and winter.*—About three weeks at temperatures ranging from 20C to 35C.

*Time to produce a rooted young plant, summer.*—About 20 to 25 days at temperatures ranging from 20C to 35C.

*Time to produce a rooted young plant, winter.*—About 25 to 30 days at temperatures ranging from 20C to 25C.

*Root description.*—Thick, fleshy; typically white in color, actual color of the roots is dependent on substrate composition, water quality, fertilizers, substrate temperature and physiological age of roots.

*Rooting habit.*—Low branching; medium density.

Plant description:

*Plant and growth habit.*—Broadly upright plant habit; broadly oblong to obovate in overall shape; moderately vigorous to vigorous growth habit and moderate growth rate; freely branching habit; dense and bushy appearance.

*Plant height, soil level to top of foliar plane.*—About 102 cm.

*Plant height, soil level to top of floral plane.*—About 64 cm.

*Plant diameter (spread).*—About 47.6 cm.

*Lateral branch description.*—Branching habit: Freely branching habit, typically about eight lateral branches per plant; pinching enhances lateral branch development. Length: About 32.6 cm. Diameter: About 3 mm. Internode length: About 4.9 cm. Aspect: Erect to about 30 degrees from vertical. Strength: Strong. Texture and luster: Smooth, glabrous; slightly glossy; becoming woody with development. Color, developing: Close to 144A. Color, developed: Close to a blend of 144A and 146C; when woody, close to N199C and 200D.

Leaf description:

*Arrangement.*—Opposite, simple.

*Length.*—About 8.2 cm.

*Width.*—About 4.5 cm.

*Shape.*—Broadly elliptic to close to broadly oblong.

*Apex.*—Short apiculate.

*Base.*—Truncate to rounded.

*Margin.*—Entire.

*Texture and luster, upper surface.*—Smooth, glabrous; slightly coriaceous; moderately glossy.

*Texture and luster, lower surface.*—Smooth, glabrous; slightly coriaceous; glossy.

*Venation pattern.*—Pinnate.

*Color.*—Developing leaves, upper surface: Slightly darker than 143A. Developing leaves, lower surface: Close to 146B. Full expanded leaves, upper surface: Darker than a blend of NN137A and 147A; venation, close to 143C. Fully expanded leaves, lower surface: Close to a blend of 146B and 147B; venation, close to 145C.

*Petioles.*—Length: About 9.5 mm. Diameter: About 2 mm by 2.5 mm. Strength: Moderately strong. Texture and luster, upper and lower surfaces: Smooth, glabrous; slightly glossy. Color, upper surface: Close to 144B; margins, close to 143B. Color, lower surface: Close to 144C; margins, close to 143B.

Flower description:

*Flower type and flowering habit.*—Single salverform flowers arranged in terminal and axillary cymes; flowers face outwardly to slightly upright; freely flowering habit with about four or five flowers per inflorescence and about 54 flower buds and open flowers developing per plant during the flowering season.

*Natural flowering season.*—Plants flower continuously from spring into the autumn in Germany; plants begin flowering about ten weeks after propagation (dependent on light level).

*Flower longevity on the plant.*—Individual flowers last about ten days; flowers not persistent.

*Fragrance.*—None detected.

*Inflorescence height.*—About 11 cm.

*Inflorescence diameter.*—About 11.5 cm.

*Flower buds.*—Length: About 5.2 cm. Diameter: About 8 mm. Shape: Narrowly oblanceolate. Texture and luster: Smooth, glabrous; slightly glossy. Color: Close to a blend of 145B and 145C; towards the apex, close to 150D; and towards the base, close to 145A.

*Flowers.*—Appearance: Flared trumpet, corolla fused and five-parted. Diameter: About 7.5 cm by 7.5 cm. Depth (length): About 5.8 cm. Throat diameter: About 1.4 cm. Tube length: About 3.9 cm. Tube diameter: Proximally, about 4 mm; distally, about 1.5 cm.

*Corolla.*—Quantity and arrangement: Five petals arranged in a single whorl; lower 50% portion of the petals are fused into a funnelform tube. Petal length, free lobes: About 4 cm. Petal width, free lobes: About 3.3 cm. Petal shape and appearance: Unequal broadly spatulate; slightly convex. Petal apex: Short apiculate, unequal. Petal margin: Entire; moderately undulate. Petal texture and luster, upper surface: Smooth, glabrous; moderately velvety; slightly glossy. Petal texture and luster, lower surface: Smooth, glabrous; slightly velvety; slightly glossy. Throat texture: Smooth, glabrous; velvety. Tube texture: Smooth, glabrous; slightly velvety. Color: Petal, when opening, upper surface: Close to NN155D; towards the throat, close to 157B to 157D and at the throat, close to 145C. Petal, when opening, lower surface: Close to NN155D; towards the base, close to 157B to 157D and at the base, close to 145C. Petal, fully opened, upper and lower surfaces: Close to NN155D; venation, close to NN155D; color does not change with subsequent development. Throat: Distally, close to 13A; mid-section, close to 17A; at the base of the throat, close to 145B; venation, similar to lamina colors. Tube: Distally, close to 155C and proximally, close to a blend of 145B and 145C; venation, similar to lamina colors.

*Sepals.*—Quantity and arrangement: Five sepals arranged in a single whorl. Length: About 8 mm. Width: About 2 mm. Shape: Lanceolate. Apex: Narrowly acuminate. Base: Broadly cuneate and fused. Margin: Entire. Texture and luster, upper surface: Smooth, glabrous; slightly glossy. Texture and luster, lower surface: Smooth, glabrous; matte. Color: When developing, upper surface: Close to 145B; towards the apex, close to 180A. When developing, lower surface: Close to 145A; towards the apex, close to 180A. Fully opened, upper surface: Close to 145A to 145B; towards the apex, close to 180A. Fully opened, lower surface: Close to 145B; towards the apex, close to 180A.

*Peduncles.*—Length: About 4.8 cm. Diameter: About 2 mm. Strength: Strong. Aspect: About 30 degrees from lateral branch axis. Texture and luster: Smooth, glabrous; moderately glossy. Color: Close to 143B.

*Pedicels.*—Length: About 1.3 cm. Diameter: About 2 mm. Strength: Strong. Aspect: About 30 degrees from peduncle axis. Texture and luster: Smooth, glabrous; moderately glossy. Color: Close to a blend of 144C and 145A.

*Reproductive organs.*—Stamens: Quantity and arrangement: Typically five; basifixed; anthers connivent. Filament length: About 2 mm. Filament color: Slightly lighter than 153D. Anther shape: Narrowly oblong. Anther size: About 1.25 mm by 8 mm. Anther color: Close to 162C and 162D. Pollen amount: None observed. Pistils: Quantity: Typically one. Pistil length: About 2 cm. Style length: About 1.8 cm. Style color: Close to 151D. Stigma diameter: About 2 mm. Stigma shape: Club-shaped, pointed. Stigma color: Close to 146D. Ovary color: Close to 143C.

*Seeds and fruits.*—To date, seed and fruit production have not been observed on plants of the new *Mandevilla.*

Pathogen & pest resistance: To date, plants of the new *Mandevilla* have not been noted to be resistant to pathogens and pests common to *Mandevilla* plants.

Temperature tolerance: Plants of the new *Mandevilla* have been observed to tolerate temperatures ranging from about 5C to about 40C and to be suitable for USDA Hardiness Zones 9 to 13.

It is claimed:

1. A new and distinct *Mandevilla* plant named 'Inmanbewhi22' as illustrated and described.

* * * * *